(12) United States Patent
Pageat (10) Patent No.: US 10,258,593 B2
(45) Date of Patent: *Apr. 16, 2019

(54) SEMIOCHEMICAL COMPOSITIONS TO REDUCE SOCIAL CONFLICTS WITH CATS

(71) Applicant: INSTITUT DE RECHERCHE EN SEMIOCHIMIE ET ETHOLOGIE APPLIQUEE, Saint Saturnin d'apt (FR)

(72) Inventor: Patrick Pageat, Apt (FR)

(73) Assignee: INSTITUT DE RECHERCHE EN SEMIOCHIMIE ET ETHOLOGIE APPLIQUEE, Saint Saturnin d'Apt (FR)

( * ) Notice: Subject to any disclaimer, the term of this patent is extended or adjusted under 35 U.S.C. 154(b) by 114 days.

This patent is subject to a terminal disclaimer.

(21) Appl. No.: 15/127,060

(22) PCT Filed: Mar. 17, 2015

(86) PCT No.: PCT/IB2015/000633
§ 371 (c)(1),
(2) Date: Sep. 19, 2016

(87) PCT Pub. No.: WO2015/140637
PCT Pub. Date: Sep. 24, 2015

(65) Prior Publication Data
US 2018/0169053 A1   Jun. 21, 2018

Related U.S. Application Data

(60) Provisional application No. 61/954,785, filed on Mar. 18, 2014.

(51) Int. Cl.
| A61K 45/06 | (2006.01) |
| A61K 47/10 | (2017.01) |
| A61K 31/215 | (2006.01) |
| A61K 31/225 | (2006.01) |
| A61K 31/231 | (2006.01) |

(52) U.S. Cl.
CPC .......... *A61K 31/231* (2013.01); *A61K 31/215* (2013.01); *A61K 31/225* (2013.01); *A61K 45/06* (2013.01); *A61K 47/10* (2013.01); *A61K 2300/00* (2013.01)

(58) Field of Classification Search
USPC ....................................................... 514/547
See application file for complete search history.

(56) References Cited

U.S. PATENT DOCUMENTS 6,054,481 A    4/2000 Pageat

FOREIGN PATENT DOCUMENTS

| EP | 1047415 | 12/2004 |
| GB | 2483732 | 3/2012 |
| JP | 11-209293 | 8/1999 |
| WO | 96/23414 A1 | 8/1996 |
| WO | 99/37297 A1 | 7/1999 |
| WO | WO 2009/144321 | 12/2009 |
| WO | 2014/001836 A1 | 1/2014 |

OTHER PUBLICATIONS

International Search Report (ISR), dated Sep. 25, 2015, from corresponding PCT Application No. PCT/IB2015/000633.
International Preliminary Report on Patentability (IPRP), dated Sep. 20, 2016, from corresponding PCT Application No. PCT/IB2015/000633.
Japanese Office Action dated Mar. 6, 2018 in corresponding Japanese Patent Application No. 2017-500455 with English language translation of Japanese Office Action.

*Primary Examiner* — Kathrien A Cruz
(74) *Attorney, Agent, or Firm* — Young & Thompson (57) ABSTRACT

A semiochemical composition including methyl laurate, methyl myristate, methyl palmitate, methyl linoleate, methyl oleate, methyl stearate, dimethyl pimelate, dimethyl azelate, salts thereof, derivatives thereof, isomers thereof and/or structural analogs thereof that maintain their semiochemical capabilities is described. Methods to reduce social conflicts in multi-cat households or in catteries or kennels boarding cats are also disclosed, as well as methods for inducing social facilitation in cats.

16 Claims, 4 Drawing Sheets

FIGURE 1

ANALOGICAL VISUAL SCALES TO BE FILLED OUT BY THE DIFFERENT OWNERS

Date___________ Scheduled time___________

Name and surname of the person:

1. A number of studies that show aggression between cats that live together in the same house and this is noticed by their owners. Please give us your perception by placing a vertical line on the two analogical visual scales below.

AVS 1

Aggressiveness

The cats never stop fighting when they are |________________________| longer together (threats, scratching, biting)

cats do not fight any (threats, scratching, biting)

AVS 2

Affiliation

I am not confident to let my cats together in the same room |________________________| let my cats together I am totally confident to let my cats together in the same room 2. In the home were there episodes of inappropriate urination (outside the litter box):

Yes No

FIGURE 2

0=Cats never stop fighting when they are together (threat, scratching, bite)

10= Cats do not fight ever (threat, scratching, bite)

FIGURE 3

AVS 2

AFFILIATION

0 = Not confident to let cats together in the same room
10 = Totally confident to let cats together in the same room

FIGURE 4

For AVS 1: 0=Cats never stop fighting when they are together (threat, scratching, bite)

10= Cats do not fight ever (threat, scratching, bite)

For AVS 2: 0=Not confident to let cats together in the same room

10=Totally confident to let cats together in the same room

SEMIOCHEMICAL COMPOSITIONS TO REDUCE SOCIAL CONFLICTS WITH CATS

FIELD OF THE INVENTION

The present invention relates to a semiochemical composition comprising methyl laurate, methyl myristate, methyl palmitate, methyl linoleate, methyl oleate, methyl stearate, dimethyl pimelate, dimethyl azelate, salts thereof, derivatives thereof, isomers thereof and/or structural analogs thereof that maintain their semiochemical capabilities and mixtures thereof. Methods to reduce social conflicts in multi-cat households or in catteries or kennels boarding cats are also disclosed, as well as methods for inducing social facilitation in cats.

BACKGROUND AND PRIOR ART

Felidae are known to be solitary predators and they generally do not live in socially structural groups, with the exception of lions. Cats travel alone, hunt alone and only associate with other adult cats for mating. Domestic cats tend to be solitary and do not form large complex social groups. Cats are also very territorial by nature and mark their territory using scent derived from facial glands, feces, urine and anal glands. This territorial marking helps the cat to communicate with other cats and to minimize direct conflict. If another cat encroaches its marked territory an aggressive interaction is maintained by the cat to chase the invading cat off its territory by staring, hissing and growling and if this does not happen to work, through a short noisy violent physical attack. Cats do not invest energy in maintaining social bonds nor do they reconciliate after a conflict (Van den Bos (1998) Post-conflict stress-response in confined group-living cats (*Felis sylvetris catus*). *Applied Animal Behaviour Science* 59:323-330.

Cats are not aggressive for any reason. There are in fact causes for the aggressiveness, as well as different type of aggression such as intercat aggression caused when two or more cats have a hostile relationship with each other; redirected aggression caused when the cat hears or sees something that it cannot have access to; petting-induced aggression caused by petting beyond the cats tolerance; fear aggression caused when the cat feels backed in a corner with no way out; play-related aggression caused while the cats plays; territorial aggression caused when another animal invades the cats territory; pain-induced aggression caused when one touches a hurting or injured spot on the cat; maternal aggression caused when a cat's kitten is threatened; and unprovoked aggression caused for no reason whatsoever.

Aggressive behavior in cats is often encountered when there are several cats in a sole household that are unfamiliar with each other or when the cats are at a catterie or kennel boarding cats with other unfamiliar cats. Thus it is well known that when a new cat is brought into a household having other cats friction between these felines very often occurs. This is especially true when cats live indoors and are forced to live in close proximity to each other which is foreign to the cat's nature and forces cats into an unnatural social arrangement. Behavioral problems often arise such as territorial urine marking and infighting to establish a dominance controlled hierarchy. In many cases the less dominant cat can develop chronic stress which can result in idiopathic cystitis. In some cases the cat can become a social outcast and won't come out of hiding for meals or to eliminate.

The critical period for a cat's socialization to conspecifics and humans is between two to eight weeks postpartum (Jongman, E C (2007) Adaptation of domestic cats to confinement. *Journal of Veterinary Behavior* 2; 1920196). Cats that do not have adequate interactions during this period with conspecifics become socially dysfunctional and have inappropriate behavior towards other cats. Poorly socialized cats are more stressed than socialized cats in multi-cat households and have a negative affect on the rest of the group by increasing the other cats stress levels (Kessler M R and Turner D C (1999a) Effects of density and cage size on stress in domestic cats (*Felis sylvetris catus*) housed singly, in pairs and in groups in boarding catteries. *Animal Welfare* 6:243-254).

Semiochemicals are chemicals emitted by a plant or an animal that evokes a behavioral or physiological response in another organism. When the semiochemical affects an individual of the same species, it is called a pheromone. When the semiochemical affects an individual of a different species, it is called an allelochemical.

Pheromones are substances released by the body of particular species that cause a predictable reaction by another individual of the same species, which may serve, for example, as a specific attractant, social communicator, sexual stimulant, appeasement and effects basic animal behavior. There are different types of pheromones such as aggregation pheromones that function in defense against predators, mate selection and overcoming host resistance by massive attack; alarm pheromones, which are released when attacked by a predator; epideictic pheromones, which are recognized by insects for signaling other insect that they should clutch elsewhere; releaser pheromones, which are attractant pheromones that some organisms use to attract mates from a distant of two miles or more; signal pheromones, which cause short term changes such as releasing a neurotransmitter which activates a response; primer pheromones, which trigger a change of developmental events; territorial pheromones, which mark the boundary of an animal's territory; trail pheromones, prevalent in insects, such as ants that lay down pheromones as they return to their nest with food; information pheromones, which are indicative of an animal's identity or territory; sex pheromones, which indicate the availability of the female for breeding; cats' facial pheromones that prevents cats from urinating on a marked spot or to prevents anxiety in cats or to familiarize cats in a new environment; and appeasement pheromones, which decrease stress, anxiety and aggressiveness in animals.

U.S. Pat. No. 5,709,863 discloses a composition comprising an emulsion comprising a mixture of oleic acid, azaleic acid, pimelic acid, and palmitic acid, said mixture capable of preventing cats from urinating in a marked spot; and a compound of vegetal origin that has an attractive effect on cats. It does not describe a semiochemical to reduce social conflicts in cats and/or to improve social facilitation in multi-cat households or catteries or in kennels boarding multiple cats.

U.S. Pat. Nos. 6,054,481, 6,077,867, 6,169,113, 6,384,252 and 7,723,388 all describe various mammalian and avian appeasing pheromones. However none of these patents describe the management of social conflicts and/or to improve social facilitation in multi-cat households or catteries or kennels that board cats.

It is thus an object of the present invention to provide semiochemical compositions for the management of social conflicts in multi-cat households or catteries or kennels that board cats.

Yet another object of the present invention is to provide a method to reduce social conflicts in multi-cat households or catteries or kennels that board cats.

In yet another object is to provide a method to induce social facilitation of cats in multi-cat households or catteries or kennels that board cats.

These and other objects are achieved by the present invention as evidenced by the summary of the invention, the description of the preferred embodiments and the claims.

SUMMARY OF THE INVENTION

The present invention provides a semiochemical composition comprising methyl laurate, methyl myristate, methyl palmitate, methyl linoleate, methyl oleate, methyl stearate, dimethyl pimelate, dimethyl azelate, salts thereof, derivatives thereof, isomers thereof and/or structural analogs thereof that maintain their semiochemical capabilities.

A semiochemical composition comprising a mixture of methyl laurate, methyl myristate, methyl palmitate, methyl linoleate, methyl oleate, methyl stearate, dimethyl pimelate, dimethyl azelate, salts thereof, derivatives thereof, isomers thereof and/or structural analogs thereof that maintain their semiochemical capabilities is also encompassed by the present invention.

In another aspect a semiochemical composition is provided comprising between about 1% to 8% (w %/w %) methyl laurate, between about 1% to 8% (w %/w %) methyl myristate, between about 10% to 18% (w %/w %) methyl palmitate, between about 3% to 10% (w %/w %) methyl linoleate, between about 40% to 55% (w %/w %) methyl oleate, between about 1% to 8% (w %/w %) methyl stearate, between about 5% to 15% (w %/w %) dimethyl pimelate, between about 4% to 15% (w %/w %) dimethyl azelate, salts thereof, derivatives thereof, isomers thereof and/or structural analogs thereof that maintain their semiochemical capabilities.

A semiochemical composition is provided comprising a mixture of between about 1% to 8% (w %/w %) methyl laurate, between about 1% to 8% (w %/w %) methyl myristate, between about 10% to 18% (w %/w %) methyl palmitate, between about 3% to 10% (w %/w %) methyl linoleate, between about 40% to 55% (w %/w %) methyl oleate, between about 1% to 8% (w %/w %) methyl stearate, between about 5% to 15% (w %/w %) dimethyl pimelate, between about 4% to 15% (w %/w %) dimethyl azelate, salts thereof, derivatives thereof, isomers thereof and/or structural analogs thereof that maintain their semiochemical capabilities.

A semiochemical composition comprising between about 2% to 6% (w %/w %) methyl laurate, between about 2% to 6% (w %/w %) methyl myristate, between about 11% to 15% (w %/w %) methyl palmitate, between about 4% to 8% (w %/w %) methyl linoleate, between about 42% to 50% (w %/w %) methyl oleate, between about 2% to 6% (w %/w %) methyl stearate, between about 7% to 13% (w %/w %) dimethyl pimelate, between about 6% to 11% (w %/w %) dimethyl azelate, salts thereof, derivatives thereof, isomers thereof and/or structural analogs thereof that maintain their semiochemical capabilities is yet another embodiment of the invention.

A semiochemical composition comprising a mixture of between about 2% to 6% (w %/w %) methyl laurate, between about 2% to 6% (w %/w %) methyl myristate, between about 11% to 15% (w %/w %) methyl palmitate, between about 4% to 8% (w %/w %) methyl linoleate, between about 42% to 50% (w %/w %) methyl oleate, between about 2% to 6% (w %/w %) methyl stearate, between about 7% to 13% (w %/w %) dimethyl pimelate, between about 6% to 11% (w %/w %) dimethyl azelate, salts thereof, derivatives thereof, isomers thereof and/or structural analogs thereof that maintain their semiochemical capabilities is yet another embodiment of the invention.

The semiochemical compositions, as described herein, further comprise an acceptable vehicle. This acceptable vehicle is a pharmaceutically acceptable vehicle or a veterinarian acceptable vehicle.

The semiochemical compositions, as described herein, can further comprise a nontoxic filler or an enhancer composition. The nontoxic filler is selected from the group of fatty acids, alcohols, amines, squalene, glycerol and mixtures thereof, while the enhancer composition contains amines and fatty acids from indolic derivatives, esters of these amines and fatty acids, ketones, acetone, alcohols or sterols.

In yet another aspect the semiochemical compositions, as described herein, are an ester, an alcohol, a ketone, an amide, an ether, an aldehyde or a sterol derivative of methyl laurate, methyl oleate, methyl myristate, methyl palmitate, methyl linolate, methyl linoleate, methyl stearate, dimethyl pimelate, dimethyl azelate, salts thereof, isomers thereof and/or structural analogs thereof that maintain their semiochemical capabilities and mixtures thereof.

A solution comprising the semiochemical composition, as described herein, and a solvent is yet another aspect of the invention. The solution is in the form of a spray, an aerosol, is administered in diffuser, is microencapsulated or is a slow release matrix.

A method to reduce social conflicts in multi-cat households or in catteries or kennels said method comprising releasing said semiochemical composition, as described herein, or the solution, as described herein, in an environment surrounding cats is another aspect of the invention. In this embodiment, the semiochemical composition or said solution is released slowly. This release occurs between 3 to 5 weeks or 4 to 6 weeks and is generally in an indoor environment or an enclosed environment.

In another aspect the present invention provides a method for inducing social facilitation in cats said method comprising releasing said semiochemical compositions, as described herein, or the solution, as described herein, in an environment surrounding cats. In this embodiment, the semiochemical composition or said solution is released slowly. This release occurs between 3 to 5 or 4 to 6 weeks and is generally in an indoor environment or an enclosed environment.

A semiochemical composition, as described herein, for use in reducing social conflicts in catteries or kennels containing cats or in multi-cat households is another aspect of the invention.

A semiochemical composition, as described herein, for use in inducing social facilitation in cats is yet another aspect of the present invention.

BRIEF DESCRIPTION OF THE DRAWINGS

The scale 10 means that the cats do not ever fight. There was no significant difference between the two groups of treatment at day 0 (AVS aggression $z=0.868$; $p=0.385$; Mann Whitney test), but there was a significant improvement between the scores day 0 and day 30 $df=3$; $F=4.24$; $p=0.01$; ANOVA).

FIG. 3 is a graph showing the final results from the affiliation analysis from the study over 30 days. The scale 0 means that the cat's owners were not confident to let their cats together in the same room. The scale 10 means that the cat's owners were confident to let their cats together in the same room. There was no significant difference between the two groups of treatment at day 0 (AVS affiliation $z=-0.172$; $p=0.862$; Mann Whitney test), but there was a significant improvement between the scores day 0 and day 30 $df=3$; $F=5.49$; $p=0.003$; ANOVA).

DETAILED DESCRIPTION OF THE PREFERRED EMBODIMENTS

As used herein the word "cat" encompasses any member of the family Felidae including the common domestic cats as well as feral cats, tigers, lions, leopards, mountain lions, lynx, bobcats, cheetahs, ocelots and the like.

As used herein "semiochemical" means a chemical emitted by a plant or an animal that evokes a behavioral or physiological response in another organism. When the semiochemical affects an individual of the same species, it is called a pheromone. When the semiochemical affects an individual of a different species, it is called an allelochemical.

"That maintain their semiochemical capabilities" means that the semiochemical composition reduces social conflicts in cats in multi-cat households, in catteries or in kennels containing cats. This is evidenced by the cats behavior which shows less aggressiveness to other cats and/or can be left together in the same room. It also includes inducing social facilitation in cats such that cats, for example eat together.

As used herein "aggressiveness in cats is when cats bite, scratch or threaten another cat by stalking, staring, yowling, howling and/or puffing up their fur.

By "social facilitation" is meant that cats that live together in a household are familiar, affiliated and friendly with one another and share a group scent.

By "stress-associated disease," as used herein, is meant any disease whose symptoms increase due to stress.

As used herein by "structural analogues" is meant any compound that has a structure similar to that of another but differs in one or more functional groups, atoms, or substructures which are replaced with other functional groups, atoms, or substructures. For instance, replacement of methyl groups with heteroatoms in the methyl fatty acids, described herein.

"Derivatives" as used herein include esters, alcohols, ketones, amides, ethers, aldehydes and sterols of the methyl esters of the fatty acids of methyl laurate, methyl myristate, methyl palmitate, methyl linolate, methyl linoleate, methyl stearate, methyl oleate, dimethyl pimelate, dimethyl azelate, salts thereof, derivatives thereof, isomers thereof and/or structural analogs thereof and mixtures of methyl esters of the fatty acids of palmitate, linoleate, oleate, stearate, laurate, myristate, as well as structural analogs thereof and/or salts thereof. These methylated fatty acid derivatives can replace one or more of the fatty acids in the composition, as described herein, and have the same effects.

"Isomers" includes structural isomerism and spatial isomerism and refers to the methyl esters of the fatty acids of palmitate, linoleate, oleate, stearate, laurate, myristate, dimethyl pimelate, dimethyl azelate as well as salts thereof, derivatives thereof and/or structural analogs that maintain the pheromonal appeasement activity and/or social facilitation activity thereof and mixtures of methyl esters of the fatty acids of palmitate, linoleate, oleate, stearate, laureate, myristate, as well as structural analogs thereof that maintain the semiochemical activity and/or social facilitation activity, salts thereof and/or derivatives thereof.

As used herein the term "mixtures" encompasses the methyl esters of the fatty acids of palmitate, linoleate, oleate, stearate, laurate, myristate, dimethyl pimelate, dimethyl azelate as well as salts thereof, derivatives thereof, isomers thereof and/or structural analogs thereof that maintain the semiochemical activity and/or social facilitation activity in which the methyl esters of the fatty acids, as described herein, can be replaced with their salts and/or derivatives and/or isomers and/or structural analogs thereof that maintain the semiochemical activity and/or social facilitation activity. For example, the mixture can comprise the methyl ester of palmitate and the methyl ester of linoleate, derivatives of oleate and stearate, isomers of methyl laurate dimethyl pimelate and dimethyl azelate and a structural analogue of myristate.

The term "solution" is meant a solid or oil that is dispersed in a liquid either by being dissolved or in suspension.

The term "releasing" means to deliver the semiochemical composition, as described herein, or the solution, as described herein.

By "environments surroundings cats" is meant any surroundings in which the cats are present including houses, apartments, rooms, cages, enclosed porches and the like.

As used herein "reduce social conflicts in cats" means to lower the aggressiveness of cats for other cats.

"Released slowly" means that the semiochemical composition, as described herein, or the solution, as described herein, is released over a period of time and not at once. The time period may vary from 3 to 5 weeks or 4 to 6 weeks.

By "acceptable vehicle" is meant any pharmaceutically acceptable vehicle or veterinary vehicle that does not interfere with the activity of the cat appeasing pheromone composition and is not toxic to the cats to which it is administered. It includes solvents, dispersion media, absorption delaying agents and the like. These pharmaceutically acceptable vehicles are described in Remington's Pharmaceutical Sciences $21^{st}$ edition 2005. An acceptable vehicle can be, for example, glycol ethers. It can be added to the cat appeasing pheromone during formulation.

By "enhancer composition" is meant an active semiochemical composition or analogues thereof that is species-specific in cats and which can be used to enhance or act synergistically with the basic semiochemical composition, as described herein, salts and/or analogues thereof to increase the effectiveness in felines of the basic semiochemical composition or analogues thereof.

By "consisting essentially of" means that the compositions contain all of the methyl ester fatty acids, salts thereof, derivatives thereof and isomers thereof and/or structural analogues, as described herein, as well as other additives that do not affect the semiochemical nature of the compositions.

More specifically, the present invention relates to the identification and synthesis of cat semiochemicals that are used to reduce social conflicts or induce social facilitation in cats. These compositions are made up of volatile molecules, the essential components being fatty acid methyl esters comprising methyl laurate, methyl myristate, methyl palmitate, methyl linoleate, methyl oleate, methyl stearate, dimethyl pimelate, dimethyl azelate, salts thereof, derivatives thereof, isomers thereof and/or structural analogues thereof that maintain their semiochemical capabilities.

In another aspect a semiochemical composition is provided comprising between about 1% to 8% (w %/w %) methyl laurate, between about 1% to 8% (w %/w %) methyl myristate, between about 10% to 18% (w %/w %) methyl palmitate, between about 3% to 10% (w %/w %) methyl linoleate, between about 40% to 55% (w %/w %) methyl oleate, between about 1% to 8% (w %/w %) methyl stearate, between about 5% to 15% (w %/w %) dimethyl pimelate, between about 4% to 15% (w %/w %) dimethyl azelate, salts thereof, derivatives thereof, isomers thereof and/or structural analogs thereof that maintain their semiochemical capabilities.

A semiochemical composition comprising between about 2% to 6% (w %/w %) methyl laurate, between about 2% to 6% (w %/w %) methyl myristate, between about 11% to 15% (w %/w %) methyl palmitate, between about 4% to 8% (w %/w %) methyl linoleate, between about 42% to 50% (w %/w %) methyl oleate, between about 2% to 6% (w %/w %) methyl stearate, between about 7% to 13% (w %/w %) dimethyl pimelate, between about 6% to 11% (w %/w %) dimethyl azelate, salts thereof, derivatives thereof, isomers thereof and/or structural analogs thereof that maintain their semiochemical capabilities is yet another embodiment of the invention.

The concentration of the semiochemical composition in the final product can range from about 0.1% (w %/w %) to about 10% (w %/w %). In another aspect the concentration of the semiochemical composition in the final product can range from about 0.3% (w %/w %) to about 4% (w %/w %). %). In another aspect the concentration of the semiochemical composition in the final product can range from about 0.4% (w %/w %) to about 1% (w %/w %).

More specifically the semiochemical compositions of the present invention comprises a mixture of methyl laurate, methyl myristate, methyl palmitate, methyl linoleate, methyl oleate, methyl stearate, dimethyl pimelate, dimethyl azelate, salts, derivatives and isomers as well as their structural analogues, which represents between 65% to 95% (wt %/wt %) of the total composition, the remaining ingredients being nontoxic filler compounds such as fatty acids, alcohols, amines, squalene and glycerol; more particularly, aproic acid, azelaic acid, propanoic acid, geraniol, octadecatrinol, hexacosanol, trimethyl amine and methyl amine.

An enhancer composition comprising between 5% to 35% (w %/w %) can also be added to the semiochemical composition, if desired. This enhancer composition comprises volatile organic compounds and mixtures thereof. This enhancer may be species-species specific in nature. The compounds that can be used in the enhancer composition include, but are not limited to amines and fatty acids from indolic derivatives, esters of these amines and fatty acids, ketones such as acetone, alcohols, sterols and the like.

The cat appeasing semiochemical composition can be attached to a chemical carrier provided that the bioactive structure of the fatty acid methyl esters is preserved. Such carrier molecules include crown compounds, liposomes and carrier proteins.

The pharmaceutically acceptable salts of the cat semiochemical compositions that are used in the compositions, described herein, include those that are organic or inorganic salts of the fatty acid esters of methyl palmitate, methyl linoleate, methyl oleate, methyl stearate, methyl laurate, methyl myristate, dimethyl pimelate and dimethyl azelate. These are well known and described in the Physician's Desk Reference, The Merck Index and Goodman and Gilman's The Pharmacological Basis of Therapeutics. The pharmaceutically acceptable salts are, for example, sodium, potassium, ammonium, calcium and magnesium and salts formed with inorganic acids such as hydrochloric acid, hydrobromic acid, phosphoric acid, sulfuric acid and the like or salts formed with organic acids such as oxalic acid, fumaric acid, tartaric acid, malonic acid, acetic acid, citric acid, benzoic acid and the like.

The semiochemical compositions can also comprise an acceptable vehicle. This acceptable vehicle can be a pharmaceutically acceptable vehicle or a veterinarian acceptable vehicle. The pharmaceutically acceptable vehicle can be any acceptable carrier or vehicle that does not interfere with the pharmaceutical or veterinary activity of the composition and is not toxic to cats to it is administered. It includes solvents, dispersion media, coatings, absorption delaying agents and the like. These pharmaceutically acceptable vehicles are described in Remington's Pharmaceutical Sciences $22^{nd}$ edition 2012. An acceptable vehicle can be, for example, saline, buffered saline and the like. It can be added to the composition after its formulation.

In yet another aspect the semiochemical compositions, as described herein, is an ester, an alcohol, a ketone, an amide, an ether, an aldehyde or a sterol derivative of methyl laurate, methyl myristate, methyl palmitate, methyl linolate, methyl linoleate, methyl stearate, methyl oleate, dimethyl pimelate, dimethyl azelate, salts thereof, isomers thereof and/or structural analogs thereof that maintain their semiochemical capabilities and mixtures thereof.

A solution comprising the semiochemical composition, as described herein, and a solvent is yet another aspect of the invention. Solvents such as propylene glycol, alcohol, ether, chloroform, ethanol benzene, carbon disulfide, propyl alcohol, isopropanol, 2-propanol, fixed and volatile oils, diethylene glycol monoethyl ether, diethylene glycol monomethyl ether, diethylene glycol monopropyl ether, diethylene glycol monoisopropyl ether, diethylene glycol monobutyl ether, diethylene glycol monophenyl ether, diethylene glycol monobenzyl ether, diethylene glycol dimethyl ether, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether or ethylene glycol dimethyl ether and the like.

The solution is in the form of a spray, an aerosol, is administered in a diffuser, is microencapsulated or is a slow release matrix or a spray. It can also be in the form of a cat collar which releases the semiochemical at a slow rate.

A method to reduce social conflicts in multi-cat households by releasing said semiochemical composition, as described herein, or the solution containing the semiochemical composition, as described herein, is encompassed by the present invention. In this aspect, the multi-cat households have at least two cats. The semiochemical composition, as described herein, or said solution, as described herein, is released slowly into the environment surrounding cats. This slow release occurs between 4 to 6 weeks. In another aspect the slow release occurs between 3 to 5 weeks.

The environment is an indoor environment or an enclosed environment. Some examples of enclosed environments include pet carriers, enclosed rooms, animal pens and enclosed porches.

A method to reduce social conflicts in catteries or kennels containing cats said method comprising releasing said semiochemical composition, as described herein or the solution containing the semiochemical composition, as described herein, in an environment surrounding cats. The semiochemical composition, as described herein, or said solution, as described herein is released slowly into the environment surrounding cats. This slow release occurs between 4 to 6 weeks. In another aspect the slow release occurs between 4 to 6 weeks or 3 to 5 weeks.

The environment is an indoor environment or an enclosed environment. Some examples of enclosed environments include pet carriers, enclosed rooms, animal pens and enclosed porches.

In another aspect the present invention provides a method for inducing social facilitation in cats said method comprising releasing said semiochemical compositions, as described herein, or the solution containing the semiochemical composition, as described herein, in an environment surrounding cats. In this embodiment, the semiochemical composition or said solution is released slowly. This slow release occurs between 4 to 6 weeks. In another aspect the slow release occurs between 3 to 5 weeks.

The semiochemical compositions, as described herein, for use in reducing social conflicts in multi-cat households encompasses the present invention.

The semiochemical compositions, as described herein, for use in reducing social conflicts in catteries or kennels containing cats is yet another aspect of the present invention.

The semiochemical compositions, as described herein, for use in inducing social facilitation in cats is another embodiment of the present invention.

The semiochemical compositions and solutions, as described herein contain fatty acids. Fatty acids are commercially available from various companies in solid form. However, since it is difficult to solubilize fatty acids, the fatty acid is generally added to the solvent under constant agitation and at a temperature of between about 37° C. to about 38° C. more preferably about 38° C.

Once obtained, the compositions of the present invention can be tested for the efficacy to manage social conflicts in cats and/or to induce social facilitation in cats. The present semiochemical compositions were discovered after intense evaluation of the behavior of cats with different pheromones.

In order to further illustrate the present invention and advantages thereof the following specific examples are given it being understood that the same are intended only as illustrative and in nowise limitative.

EXAMPLES

Example 1—Evaluation of the Efficacy of Treatment with Semiochemical Vs. Placebo This example was to test for the aggressiveness of multi-cat households in which the cats were currently in a situation of conflict. The evaluation of the treatment which consisted of a mixture of 11.4% (wt %/wt %) of dimethyl pimelate, 7.8% (wt %/wt %) of dimethyl azelate. 35.6% (wt %/wt %) of methyl palmitate, 95.2% (wt %/wt %) methyl oleate, 11% (wt %/wt %)methyl laurate, 11% (wt %/wt %)methyl myristate, 17% (wt %/wt %)methyl linoleate and 11% methyl sterate. 0.5% (wt %/wt %) of this mixture was diluted in 99.5% isopar V as a social facilitator in multi-cat households was administered via a diffuser. Households having 2 or 3 cats for more than 1 year, were evaluated with the aid of two analogical visual scales (AVS) filled out by the cats owner at different times of the study. The two analogical visual scales (AVS) were for aggressiveness (AVS 1) and affiliation (AVS 2). The cats' owner filled out these two forms at day 0 (T0), day 10 (T1), day 20 (T2) and day 30 (T3) of the study. The control was evaluated at 60 days (T4) by telephone. T1, T2 and T3 were effectuated by telephone with the people conducting this study. The questioner containing the analogical visual scales (AVS) used in the experiment and given to the owners of multi-cat households are described in FIG. 1.

All the questioners were returned to the people conducting the study after the evaluation at day 30 (T3). At 1 month (T4) later a post-treatment evaluation by telephone was undertaken.

Eighteen households having at least two or three cats for more than 1 year and no aggression towards the owner, no aggression with wounds of the other cats and no other treatments were used in this study. Seven veterinary clinics recruited the multiple cat households or participated in the study and discussed the study and their acceptance into it by filing an agreement. This started at day 0 (T0) and called the inclusion visit.

Each owner was then provided with an electric diffuser that had either only the excipient, which was the placebo or the treatment. Instructions were also given on how to use the diffuser. The study was a multicenter, blinded placebo-controlled study having 10 placebos and 8 treatments. The diffusers were labeled 1 and 2 and were given to the cat owners depending on the surface area of the home. The diffusers covered rooms that were 500 to 700 square feet. The following Table 1 shows the distribution of the diffusers and their content:

TABLE 1

| house | Processing Code | Treatment | Diffuser content |
|---|---|---|---|
| 1 | 1 | A | placebo |
| 2 | 2 | B | treatment |
| 3 | 3 | B | treatment |
| 4 | 4 | A | placebo |
| 5 | 5 | B | treatment |
| 6 | 6 | A | placebo |
| 7 | 13 | B | treatment |
| 8 | 14 | A | placebo |
| 9 | 17 | A | placebo |
| 10 | 23 | B | treatment |
| 11 | 24 | A | placebo |
| 12 | 45/48 | A | placebo |
| 13 | 46 | B | treatment |
| 14 | 49 | B | treatment |
| 15 | 50 | A | placebo |
| 16 | 51/54 | B | treatment |
| 17 | 52 | A | placebo |
| 18 | 53 | A | placebo |

The data was collected from the 18 owners of the multi-cat household. In the case of household 13, the owner dropped out of the study after three days since the owner decided not to participate in the study. In consequence the results were excluded from the data analysis and only 17 results were analyzed.

The analysis was analyzed for 17 households as set forth in Tables 2 and 3 below.

TABLE 2 student T test

| variable | Average group A | Average Group B | t value | dl | p value | Number of actives A | Number of actives B | Standard Deviation A | Standard Deviation B |
|---|---|---|---|---|---|---|---|---|---|
| AVS 1 Day 0 | 4.000000 | 4.100000 | −.086130 | 15 | 0.932503 | 10 | 7 | 2.835881 | 1.346601 |
| AVS 1 Day 10 | 4.300000 | 4.985714 | −.484836 | 15 | 0.634797 | 10 | 7 | 3.459608 | 1.624221 |
| AVS 1 Day 20 | 5.500000 | 5.842857 | −.229643 | 15 | 0.821472 | 10 | 7 | 3.470191 | 2.209719 |
| AVS 1 Day 30 | 5.888889 | 6.414286 | −.347797 | 14 | 0.733166 | 9 | 7 | 3.352031 | 2.446377 |
| AVS 2 Day 0 | 3.490000 | 4.300000 | −.489146 | 15 | 0.631814 | 10 | 7 | 3.519612 | 3.105908 |
| AVS 2 Day 10 | 4.040000 | 5.157143 | −.715854 | 15 | 0.485077 | 10 | 7 | 3.520164 | 2.546146 |
| AVS 2 Day 20 | 5.160000 | 6.371429 | −.758726 | 15 | 0.459773 | 10 | 7 | 3.644539 | 2.513772 |
| AVS 2 Day 30 | 5.366667 | 7.028571 | −.942942 | 14 | 0.361699 | 9 | 7 | 3.744663 | 3.137257 |

The ratio of F variances and the p variances are set forth in Table 3 below based on the data from the student T test for Group A and Group B. The two analogical visual scales (AVS) were for aggressiveness (AVS 1) and affiliation (AVS 2).

TABLE 3

| Variable | Ratio of the F variance | p variance |
|---|---|---|
| AVS 1 Day 0 | 4.435049 | 0.083689 |
| AVS 1 Day 10 | 4.536943 | 0.079445 |
| AVS 1 Day 20 | 2.466225 | 0.284188 |
| AVS 1 Day 30 | 1.877453 | 0.458448 |
| AVS 2 Day 0 | 1.284140 | 0.786508 |
| AVS 2 Day 10 | 1.911434 | 0.443555 |
| AVS 2 Day 20 | 2.102005 | 0.378261 |
| AVS 2 Day 30 | 1.424706 | 0.685197 |

No significant difference was observed between Group A (placebo) and Group B (treated).

A Shapiro-Wilk test for normality was then performed on Group A and Group B. The results are shown in Table 4 below.

TABLE 4

| Variable | Group A | Group B | Normality |
|---|---|---|---|
| AVS 1 day 0 | 0.06539 | 0.33781 | Yes |
| AVS 1 day 10 | 0.01196 | 0.48727 | No |
| AVS 1 day 20 | 0.25822 | 0.47791 | Yes |
| AVS 1 day 30 | 0.49347 | 0.30573 | Yes |
| AVS 2 day 0 | 0.07433 | 0.20306 | Yes |
| AVS 2 day 10 | 0.02647 | 0.72960 | No |
| AVS 2 day 20 | 0.25541 | 0.24576 | Yes |
| AVS 2 day 30 | 0.18436 | 0.06120 | Yes |

Table 5 set forth below showed the results from a Mann-Whitney U test.

TABLE 5

| | Placebo | | | Treatment | | | | | |
|---|---|---|---|---|---|---|---|---|---|
| variable | average | median | Standard deviation | average | median | Standard deviation | U | Z | p value |
| AVS 1 Day 0 | 4.00 | 4.80 | 2.83 | 4.10 | 4.70 | 1.34 | 32.00 | 0.2439 | 0.807 |
| AVS 1 Day10 | 4.30 | 4.40 | 3.45 | 4.98 | 4.70 | 1.62 | 33.0 | −0.1463 | 0.883 |
| AVS 1 Day 20 | 5.50 | 5.70 | 3.47 | 5.84 | 5.00 | 2.20 | 33.0 | −0.1463 | 0.883 |
| AVS 1 Day 30 | 5.88 | 7.00 | 3.35 | 6.41 | 6.40 | 2.44 | 29.0 | −0.2117 | 0.832 |
| AVS 2 Day 0 | 3.49 | 2.35 | 3.51 | 4.30 | 2.60 | 3.10 | 28.0 | −0.6343 | 0.525 |
| AVS 2 Day 10 | 4.04 | 2.15 | 3.52 | 5.15 | 5.20 | 2.54 | 25.0 | −0.9271 | 0.353 |
| AVS 2 Day 20 | 5.16 | 4.60 | 3.64 | 6.37 | 7.60 | 2.51 | 31.0 | −0.3415 | 0.732 |
| AVS2 Day 30 | 5.36 | 7.10 | 3.74 | 7.02 | 9.00 | 3.13 | 21.0 | −1.0585 | 0.289 |

Tests significantly different at p<0.500

Another Mann Whitney U test was run and the results are shown in the Table below in Table 6.

TABLE 6

| Variable | Total Regression A | Total Regression B | U | z | p value | Adjusted z | p value | Number active A |
|---|---|---|---|---|---|---|---|---|
| AVS 1 day 0 | 93.00000 | 60.00000 | 32.00000 | 0.24398 | 0.807250 | 0.2442 | .806902 | 10 |
| AVS 1 day 10 | 88.00000 | 65.00000 | 33.00000 | −.14639 | 0.883618 | −.14656 | .883476 | 10 |
| AVS 1 day 20 | 88.00000 | 65.00000 | 33.00000 | −.14639 | 0.883618 | −.14656 | .883476 | 10 |
| AVS 1 day 30 | 74.00000 | 62.00000 | 29.00000 | −.21170 | 0.832339 | −.21186 | .832218 | 9 |
| AVS 2 day 0 | 83.00000 | 70.00000 | 28.00000 | −.63434 | 0.52863 | −.63550 | .525100 | 10 |
| AVS 2 day 10 | 80.00000 | 73.00000 | 25.00000 | −.92711 | 0.353873 | −.92711 | .353873 | 10 |
| AVS 2 day 20 | 86.00000 | 67.00000 | 31.00000 | −.34157 | 0.732678 | −.34177 | .732521 | 10 |
| AVS day 30 | 66.00000 | 70.00000 | 21.00000 | −1.05851 | 0.289823 | −1.05851 | .289823 | 9 |

A Mann Whitney U test was also performed for only the treated group B.

TABLE 7

| variable | Number of active B | 2*(1 − p) p exact |
|---|---|---|
| AVS 1 day 0 | 7 | 0.812526 |
| AVS 1 day 10 | 7 | 0.886775 |
| AVS 1 day 20 | 7 | 0.886755 |
| AVS 1 day 30 | 7 | 0.837063 |
| AVS 2 day 0 | 7 | 0.536199 |
| AVS 2 day 10 | 7 | 0.363842 |
| AVS 2 day 20 | 7 | 0.739613 |
| AVS 2 day 30 | 7 | 0.299126 |

There was no significant difference observed between group A and B in the treatment.

A Repeated Measures Anova statistical analysis was effectuated to evaluate the treatment factor for the four different times and the effect of time between day 0 (D0) and day 30 (D30), as well as the variations in the responses of the cats owner to the AVS and in function of time of the treatment. The results are shown in Table 8 for AVS1.

TABLE 8

| | AVS 1 | | | | |
|---|---|---|---|---|---|
| Effect | Sum of Squares | Degree of liberty | Mean square | Degree of freedom F | p value |
| Ordinate of origin | 1707.943 | 1 | 1707.943 | 69.33264 | 0.000001 |
| treatment | 1.048 | 1 | 1.048 | 0.04254 | 0.839568 |
| error | 344.877 | 14 | 24.634 | | |
| time | 39.980 | 3 | 13.327 | 5.07375 | 0.004348 |
| time of treatment | 0.595 | 3 | 0.198 | 0.07555 | 0.972826 |
| error | 110.318 | 42 | 2.627 | | |

A significant difference was observed regarding the time factor. In effect an augmentation was observed between D0 (day 0) and D30 (day 30).

A Tukey's HSD Post-hoc test was then utilized to calculate the data from the ANOVA statistical test set forth above in Table 8. The results are set forth in Table 9 below.

TABLE 9

| Cell number | treatment | time | 1 4.1111 | 2 4.6667 | 3 5.6444 | 4 5.8889 | 5 4.1000 | 6 4.9857 | 7 5.8429 | 8 6.4143 |
|---|---|---|---|---|---|---|---|---|---|---|
| 1 | A | AVS 1 day 0 | | 0.995681 | 0.489636 | 0.303788 | 1.000000 | 0.998438 | 0.922422 | 0.7444082 |
| 2 | A | AVS 1 day 10 | 0.995681 | | 0.901241 | 0.747762 | 0.999910 | 0.999998 | 0.990268 | 0.918987 |
| 3 | A | AVS 1 day 20 | 0.489636 | 0.901241 | | 0.999981 | 0956039 | 0.999756 | 1.000000 | 0.999322 |
| 4 | A | AVS 1 day 30 | 0.303788 | 0.747762 | 0.999981 | | 0.909623 | 0.998078 | 1.000000 | 0.999946 |
| 5 | B | AVS 1 day 0 | 1.000000 | 0.999910 | 0.956039 | 0.909623 | | 0.968360 | 0.486541 | 0.160145 |
| 6 | B | AVS 1 day 10 | 0.998438 | 0.999998 | 0.999756 | 0.998078 | 0.968360 | | 0.973561 | 0.718493 |
| 7 | B | AVS 1 day 20 | 0.922422 | 0.990268 | 1.000000 | 1.000000 | 0.486541 | 0.973561 | | 0.997664 |
| 8 | B | AVS 1 day 30 | 0.744082 | 0.918987 | 0.999322 | 0.999946 | 0.160145 | 0.718493 | 0.997664 | |

For AVS 2 further analysis for the repeated measures of variance was undertaken and shown in Table 10.

TABLE 10

AVS 2

| Effect | Sum of Squares | Degree of liberty | Mean square | Degree of freedom F | p value |
|---|---|---|---|---|---|
| ordinate of origin | 1685.498 | 1 | 1685.498 | 44.34161 | 0.000011 |
| treatment | 18.498 | 1 | 18.498 | 0.48664 | 0.496854 |
| error | 532.163 | 14 | 38.012 | | |
| time | 47.379 | 3 | 15.793 | 6.23770 | 0.001335 |
| time of treatment | 2.416 | 3 | 0.805 | 0.31814 | 0.812179 |
| error | 106.338 | 42 | 2.532 | | |

A significant difference was observed regarding the time factor. In effect anaugmentation was observed between D0 (day 0) and D30 (day 30).

A Tukey's HSD Post-hoc test was then utilized to calculate the data from the ANOVA statistical test set forth above in Table 10. The results are set forth in Table 11 below.

TABLE 11

| Cell number | treatment | time | 1 3.6667 | 2 4.3222 | 3 5.1667 | 4 5.3667 | 5 4.3000 | 6 5.1571 | 7 6.3714 | 8 7.0286 |
|---|---|---|---|---|---|---|---|---|---|---|
| 1 | A | AVS 2 day 0 | | 0.986915 | 0.494237 | 0.335567 | 0.999936 | 0.985107 | 0.750965 | 0.520436 |
| 2 | A | AVS 2 day 10 | 0.986915 | | 0.947367 | 0.855610 | 1.000000 | 0.999596 | 0.921349 | 0.750447 |
| 3 | A | AVS 2 day 20 | 0.494237 | 0.947367 | | 0.999995 | 0.999485 | 1.000000 | 0.995766 | 0.950741 |
| 4 | A | AVS 2 day 30 | 0.335567 | 0.855610 | 0.999995 | | 0.998030 | 1.000000 | 0.998649 | 0.972791 |
| 5 | B | AVS 2 day 0 | 0.999936 | 1.000000 | 0.999485 | 0.998030 | | 0.970745 | 0.251635 | 0.047718 |
| 6 | B | AVS 2 day 10 | 0.985107 | 0.999596 | 1.00000 | 1.000000 | 0.970745 | | 0.839301 | 0.372257 |
| 7 | B | AVS 2 day 20 | 0.750965 | 0.921349 | 0.995766 | 0.998649 | 0.251635 | 0.839301 | | 0.993737 |
| 8 | B | AVS 2 day 30 | 0.520436 | 0.750447 | 0.950741 | 0.972791 | 0.047718 | 0.372257 | 0.993737 | |

Inappropriate Urination in the Home

With respect to the results concerning inappropriate urination in the home that were recorded by the cats' owners, no significant difference was observed between the treatment and the placebo. The Fisher's exact statistical test was used in this analysis of a bilateral situation. The results are shown below in Table 12.

TABLE 12

| Day | p value |
|---|---|
| T0 (day 0-inclusion visit) | 1.0000 |
| T1 (day 10) | 1.0000 |
| T2 (day 20) | 0.3024 |
| T3 (day 30) | 0.2821 |

Chi-squared statistics were used to analysis the data for inappropriate urination in the household of multi-cat owners. Tables 13 to 16 were the results for the inappropriate urination at day 0, day 10, day 20, and day 30, respectively.

TABLE 13

| Urination at day 0 | Column 1 | Column 2 | Gross total |
|---|---|---|---|
| Effectives line 1 | 6 | 3 | 9 |
| Percentage of total | 37.500% | 18.750% | 56.250% |
| Effectives line 2 | 4 | 3 | 7 |
| Percentage of total | 25.000% | 18.750% | 43.750% |
| Total in column | 10 | 6 | 16 |
| Percentage of total | 62.500% | 37.500% | |
| $Chi^2$ (dl = 1) | 0.15 | p = .6963 | |
| $V^2$ (dl = 1) | 0.14 | p = .7055 | |
| $Chi^2$ Yates corrected | 0.02 | p = .8965 | |
| $Phi^2$ | 0.00952 | | |
| P exact Fisher, unilateral | | p = .5490 | |
| Bilateral | | p = 1.0000 | |
| $Chi^2$ McNemar (A/D) | 0.44 | p = .5050 | |
| $Chi^2$ (B/C) | 0.00 | p = 1.0000 | |

TABLE 14

| Urination at day 10 | Column 1 | Column 2 | Gross total |
|---|---|---|---|
| Effectives line 1 | 2 | 7 | 9 |
| Percentage of total | 12.500% | 43.750% | 56.250% |
| Effectives line 2 | 2 | 5 | 7 |
| Percentage of total | 12.500% | 31.250% | 43.750% |
| Total in column | 4 | 12 | 16 |
| Percentage of total | 25.000% | 75.000% | |
| $Chi^2$ (dl = 1) | .08 | p = .7711 | |
| $V^2$ (dl = 1) | .08 | p = .7782 | |
| $Chi^2$ Yates corrected | .08 | p = .7711 | |
| $Phi^2$ | .00529 | | |
| P exact Fisher, unilateral | | p = .6077 | |
| Bilateral | | p = 1.0000 | |
| $Chi^2$ McNemar (A/D) | .57 | p = .4497 | |
| $Chi^2$ (B/C) | 1.78 | p = .1824 | |

TABLE 15

| Urination at day 20 | Column 1 | Column 2 | Gross total |
|---|---|---|---|
| Effectives line 1 | 2 | 7 | 9 |
| Percentage of total | 12.500% | 43.750% | 56.250% |
| Effectives line 2 | 4 | 3 | 7 |
| Percentage of total | 25.000% | 18.750% | 43.750% |
| Total in column | 6 | 10 | 16 |

TABLE 15-continued

| Urination at day 20 | Column 1 | Column 2 | Gross total |
|---|---|---|---|
| Percentage of total | 37.500% | 62.500% | |
| $Chi^2$ (dl = 1) | 2.05 | p = .1523 | |
| $V^2$ (dl = 1) | 1.92 | p = .1658 | |
| $Chi^2$ Yates corrected | 0.83 | p = .3624 | |
| $Phi^2$ | .12804 | | |
| P exact Fisher, unilateral | | p = .1818 | |
| Bilateral | | p = .3024 | |
| $Chi^2$ McNemar (A/D) | 0.00 | p = 1.0000 | |
| $Chi^2$ (B/C) | 0.36 | p = .5465 | |

TABLE 16

| Urination at day 30 | Column 1 | Column 2 | Gross total |
|---|---|---|---|
| Effectives line 1 | 1 | 7 | 8 |
| Percentage of total | 6.667% | 46.667% | 53.333% |
| Effectives line 2 | 3 | 4 | 7 |
| Percentage of total | 20.000% | 26.667% | 46.667% |
| Total in column | 4 | 11 | 15 |
| Percentage of total | 26.667% | 73.333% | |
| $Chi^2$ (dl = 1) | 1.76 | p = .1847 | |
| $V^2$ (dl = 1) | 1.64 | p = .2001 | |
| $Chi^2$ Yates corrected | .55 | p = .4586 | |
| $Phi^2$ | .11729 | | |
| P exact Fisher, unilateral | | p = .2308 | |
| Bilateral | | p = .2821 | |
| $Chi^2$ McNemar (A/D) | .80 | p = .3711 | |
| $Chi^2$ (B/C) | .90 | p = .3428 | |

Chi-squared statistics were used to analysis the data for aggressivness in the household of multi-cat owners. The results are shown at day 10 and day 20 in Tables 17 and 18, respectively.

TABLE 17

| Aggressiveness at day 10 | Column 1 | Column 2 | Gross total |
|---|---|---|---|
| Effectives line 1 | 6 | 4 | 10 |
| Percentage of total | 35.294% | 23.529% | 58.824% |
| Effectives line 2 | 5 | 2 | 7 |
| Percentage of total | 29.412% | 11.765% | 41.176% |
| Total in column | 11 | 6 | 17 |
| Percentage of total | 64.706% | 35.294% | |

TABLE 17-continued

| Aggressiveness at day 10 | Column 1 | Column 2 | Gross total |
|---|---|---|---|
| $Chi^2$ (dl = 1) | 0.24 | p = 0.6275 | |
| $V^2$ (dl = 1) | 0.22 | p = 0.6378 | |
| $Chi^2$ Yates corrected | .00 | p = 0.9758 | |
| $Phi^2$ | .01385 | | |
| P exact Fisher, unilateral | | p = 0.5158 | |
| Bilateral | | p = 1.0000 | |
| $Chi^2$ McNemar (A/D) | 1.13 | p = 0.2889 | |
| $Chi^2$ (B/C) | 0.00 | p = 1.0000 | |

TABLE 18

| Aggressiveness at day 20 | Column 1 | Column 2 | Gross total |
|---|---|---|---|
| Effectives line 1 | 6 | 4 | 10 |
| Percentage of total | 35.294% | 23.529% | 58.824% |
| Effectives line 2 | 4 | 3 | 7 |
| Percentage of total | 23.529% | 17.647% | 41.176% |
| Total in column | 10 | 7 | 17 |
| Percentage of total | 58.824% | 41.176% | |
| $Chi^2$ (dl = 1) | .01 | p = .9062 | |
| $V^2$ (dl = 1) | .01 | p = .9090 | |
| $Chi^2$ Yates corrected | 0.15 | p = .7018 | |
| $Phi^2$ | 0.00082 | | |
| P exact Fisher, unilateral | | p = .6461 | |
| Bilateral | | p = 1.0000 | |
| $Chi^2$ McNemar (A/D) | 0.44 | p = .5050 | |
| $Chi^2$ (B/C) | 0.13 | p = .7237 | |

For day 30 of aggressiveness the $Chi^2$ test had a value of 1.0018 and the Fisher test had a value of Pr<=1.0000.

Besides the 17 households that were analyzed as set forth above the data was further analyzed for 15 households since household numbers 14 and 24 lacked certain data. In the case of household 14, AVS 1 and AVS 2 was missing for day 30 and in the case of household 24, the data for inappropriate urination for day 0 to day 30 was missing.

The data that was obtained was recalculated without household numbers 14 and 24 that lacked certain data and thus was partially incomplete. A comparison was made of the aggressive behavior and the confidence given by the owner to let their cats alone in the same room in the house.

The statistical analysis was based on the Mann Whitney U test for independent examples. The results are shown in Table 19 below.

TABLE 19

| | Placebo | | | Treatment | | | | | |
|---|---|---|---|---|---|---|---|---|---|
| variable | average | median | Standard deviation | Average | median | Standard deviation | U | Z | p value |
| AVS 1 D0 | 4.58 | 5.10 | 2.80 | 4.10 | 4.70 | 1.34 | 20.00 | 0.8679 | 0.385 |
| AVS 1 D10 | 5.02 | 7.00 | 3.51 | 4.98 | 4.70 | 1.62 | 23.00 | 0.5207 | 0.602 |
| AVS 1 D20 | 5.82 | 7.70 | 3.85 | 5.84 | 5.00 | 2.20 | 27.00 | 0.0578 | 0.953 |
| AVS 1 D30 | 5.50 | 6.10 | 3.35 | 6.41 | 6.40 | 2.44 | 24.00 | −0.4050 | 0.685 |
| AVS 2 D0 | 4.10 | 3.95 | 3.68 | 4.30 | 2.60 | 3.10 | 26.00 | −0.1735 | 0.862 |
| AVS 2 D10 | 4.66 | 4.80 | 3.70 | 5.15 | 5.20 | 2.54 | 25.00 | −0.2893 | 0.772 |
| AVS 2 D20 | 5.30 | 6.05 | 4.11 | 6.37 | 7.60 | 2.51 | 27.00 | −0.0578 | 0.953 |
| AVS2 D30 | 4.93 | 5.15 | 3.75 | 7.02 | 9.00 | 3.13 | 18.00 | −1.0994 | 0.271 |

Tests that were significant had a p<0.05000.

There was no significant difference observed between Group A (placebo) and Group B (treated).

A student T test was then performed on Groups A and B. The results are shown in Table 20 below:

TABLE 20

| Variable | Average A | Average B | t value | dl | p | Number of actives Group A | Number of actives Group B | Standard deviation Group A | Standard Deviation Group B |
|---|---|---|---|---|---|---|---|---|---|
| AVS 1 day 0 | 4.587500 | 4.100000 | 0.41865 | 13 | 0.682305 | 8 | 7 | 2.801243 | 1.346601 |
| AVS 1 day 10 | 5.025000 | 4.985714 | 0.02707 | 13 | 0.978813 | 8 | 7 | 3.512732 | 1.624221 |
| AVS 1 day 20 | 5.825000 | 5.842857 | −.01077 | 13 | 0.991571 | 8 | 7 | 3.857368 | 2.209719 |
| AVS 1 day 30 | 5.500000 | 6.414286 | −.59419 | 13 | 0.562583 | 8 | 7 | 3.359422 | 2.446377 |
| AVS 2 day 0 | 4.100000 | 4.300000 | −.11263 | 13 | 0.912046 | 8 | 7 | 3.687043 | 3.105908 |
| AVS 2 day 10 | 4.662500 | 5.157143 | −.29667 | 13 | 0.771402 | 8 | 7 | 3.703642 | 2.546146 |
| AVS 2 day 20 | 5.300000 | 6.371429 | −.59728 | 13 | 0.560580 | 8 | 7 | 4.110266 | 2.513772 |
| AVS 2 day 30 | 4.937500 | 7.028571 | −1.15094 | 13 | 0.267288 | 8 | 7 | 3.759155 | 3.137257 |

The ratio of F variances and the p variances are set forth in Table 21 below based on the data from the student T test for Group A and Group B in Table 20.

TABLE 21

| variable | Ratio F variance | p variance |
|---|---|---|
| AVS 1 day 0 | 4.327370 | 0.093954 |
| AVS 1 day 10 | 4.677347 | 0.078946 |
| AVS 1 day 20 | 3.047250 | 0.195800 |
| AVS 1 day 30 | 1.885742 | 0.457315 |
| AVS 2 day 0 | 1.409221 | 0.691911 |
| AVS 2 day 10 | 2.115883 | 0.379936 |
| AVS 2 day 20 | 2.673549 | 0.251528 |
| AVS 2 day 30 | 1.435755 | 0.675425 |

No significant difference was observed between Group A and Group B.

The normality statistical test was performed using the Shapiro-Wilk test. The following results are found in Table 22.

TABLE 22

| Variable | Group A | Group B | Normality |
|---|---|---|---|
| AVS 1 day 0 | 0.04214 | 0.33781 | No |
| AVS 1 day 10 | 0.01661 | 0.48727 | No |
| AVS 1 day 20 | 0.06299 | 0.47791 | Yes |
| AVS 1 day 30 | 0.78681 | 0.30573 | Yes |
| AVS 2 day 0 | 0.22194 | 0.20306 | Yes |
| AVS 2 day 10 | 0.09212 | 0.72960 | Yes |
| AVS 2 day 20 | 0.08154 | 0.34576 | Yes |
| AVS 2 day 30 | 0.33217 | 0.06120 | Yes |

A Mann Whitney U test was performed and the results are shown in Table 23 below.

TABLE 23

| Variable | Total Regression A | Total Regression B | U | Z | p value | Adjusted z | p value | Number active A |
|---|---|---|---|---|---|---|---|---|
| AVS 1 day 0 | 72.00000 | 48.00000 | 20.00000 | 0.86796 | 0.385419 | 0.86951 | 0.384569 | 8 |
| AVS 1 day 10 | 69.00000 | 51.00000 | 23.00000 | 0.52077 | 0.602525 | 0.52124 | 0.602200 | 8 |
| AVS 1 day 20 | 65.00000 | 55.00000 | 27.00000 | 0.05786 | 0.953857 | 0.05792 | 0.953816 | 8 |
| AVS 1 day 30 | 60.00000 | 60.00000 | 24.00000 | −0.40505 | 0.685444 | −0.40541 | 0.685178 | 8 |
| AVS 2 day 0 | 62.00000 | 58.00000 | 26.00000 | −0.17359 | 0.862187 | −0.17390 | 0.861943 | 8 |
| AVS 2 day 10 | 61.00000 | 59.00000 | 25.00000 | −0.28932 | 0.772338 | −0.28932 | 0.772338 | 8 |
| AVS 2 day 20 | 63.00000 | 57.00000 | 27.00000 | −0.05786 | 0.953857 | −0.05792 | 0.953816 | 8 |
| AVS 2 day 30 | 54.00000 | 66.00000 | 18.00000 | −1.09941 | 0.271590 | −1.09941 | 0.271590 | 8 |

Evaluation of only the treated group by the Mann-Whitney U test is set forth in Table 24 below.

TABLE 24

| variable | Number of active B | 2*(1 − p) p exact |
|---|---|---|
| AVS 1 day 0 | 7 | 0.396892 |
| AVS 1 day 10 | 7 | 0.612587 |
| AVS 1 day 20 | 7 | 0.955089 |
| AVS 1 day 30 | 7 | 0.694328 |
| AVS 2 day 0 | 7 | 0.866511 |
| AVS 2 day 10 | 7 | 0.778866 |
| AVS 2 day 20 | 7 | 0.955089 |
| AVS 2 day 30 | 7 | 0.280963 |

There was no significant difference observed between group A and B in the treatment.

An analysis using ANOVA was performed for AVS 1. The results are shown in Table 25 below.

TABLE 25

| | AVS 1 | | | | |
|---|---|---|---|---|---|
| Effect | Sum of Squares | Degree of liberty | Mean square | Degree of freedom | p value |
| Ordinate of origin | 1668.453 | 1 | 1668.453 | 64.20662 | 0.000002 |
| treatment | 0.153 | 1 | 0.153 | 0.00590 | 0.939934 |
| error | 337.814 | 13 | 25.986 | | |
| time | 25.644 | 3 | 8.548 | 4.24363 | 0.010923 |
| time of treatment | 3.862 | 3 | 1.287 | 0.63902 | 0.594467 |
| error | 78.559 | 39 | 2.014 | | |

A significant difference is observed regarding the time factor. In effect an augmentation of the AVS 1 was observed between D0 (day 0) and D30 (day 30).

A post-hoc Tukey's HSD test was then performed. The results are shown in Table 26 below.

TABLE 26

| Cell number | treatment | time | 1<br>4.5875 | 2<br>5.0250 | 3<br>5.8250 | 4<br>5.5000 | 5<br>4.1000 | 6<br>4.9857 | 7<br>5.8429 | 8<br>6.4143 |
|---|---|---|---|---|---|---|---|---|---|---|
| 1 | A | AVS 1 day 0 | | 0.998473 | 0.659686 | 0.898654 | 0.999969 | 0.999992 | 0.986767 | 0.907131 |
| 2 | A | AVS 1 day 10 | 0.998473 | | 0.946694 | 0.997409 | 0.997910 | 1.000000 | 0.999059 | 0.976650 |
| 3 | A | AVS 1 day 20 | 0.659686 | 0.946694 | | .999787 | 0.928984 | 0.998890 | 1.00000 | 0.999890 |
| 4 | A | AVS 1 day 30 | 0.898654 | 0.997409 | 0.999787 | | 0.975653 | 0.999956 | 0.999997 | 0.998065 |
| 5 | B | AVS 2 day 0 | 0.999969 | 0.997910 | 0.928984 | 0.975653 | | 0.936378 | 0.320791 | 0.071427 |
| 6 | B | AVS 2 day 10 | 0.999992 | 1.000000 | 0.998890 | 0.999956 | 0.936378 | | 0.946084 | 0.570106 |
| 7 | B | AVS 2 day 20 | 0.986767 | 0.999059 | 1.000000 | 0.999997 | 0.320791 | 0.946084 | | 0.994577 |
| 8 | B | AVS 2 day 30 | 0.907131 | 0.976650 | 0.999890 | 0.998065 | 0.071427 | 0.570106 | 0.994577 | |

The date for AVS 2 is shown in Table 27 below using Repeated Measures Anova statistical analysis.

TABLE 27

| | AVS 2 | | | | |
|---|---|---|---|---|---|
| Effect | Sum of Squares | Degree of liberty | Mean square | Degree of freedom F | p value |
| ordinate of origin | 1635.219 | 1 | 1635.219 | 40.25694 | 0.000026 |
| treatment | 13.886 | 1 | 13.886 | 0.34185 | 0.568773 |
| error | 528.054 | 13 | 40.620 | | |
| time | 31.320 | 3 | 10.440 | 5.49860 | 0.003007 |
| time of treatment | 7.787 | 3 | 2.596 | 1.36710 | 0.267056 |
| error | 74.049 | 39 | 1.899 | | |

A significant difference was observed regarding the time factor. In effect an augmentation was observed between D0 (day 0) and D30 (day 30).

A post-hoc Turkey HSD evaluation was performed and the results are shown in Table 28 below.

TABLE 28

| Cell number | treatment | time | 1<br>4.1000 | 2<br>4.6625 | 3<br>5.3000 | 4<br>4.9375 | 5<br>4.3000 | 6<br>5.1571 | 7<br>6.3714 | 8<br>7.0286 |
|---|---|---|---|---|---|---|---|---|---|---|
| 1 | A | AVS 1 day 0 | | 0.991167 | 0.661020 | 0.922389 | 1.000000 | 0.998416 | 0.890548 | 0.708945 |

TABLE 28-continued

| Cell number | treatment | time | 1<br>4.1000 | 2<br>4.6625 | 3<br>5.3000 | 4<br>4.9375 | 5<br>4.3000 | 6<br>5.1571 | 7<br>6.3714 | 8<br>7.0286 |
|---|---|---|---|---|---|---|---|---|---|---|
| 2 | A | AVS 1 day 10 | 0.991167 | | 0.981687 | 0.999915 | 0.999999 | 0.999990 | 0.972845 | 0.869503 |
| 3 | A | AVS 1 day 20 | 0.661020 | 0.981687 | | 0.999468 | 0.998900 | 1.000000 | 0.998277 | 0.971139 |
| 4 | A | AVS 1 day 30 | 0.922389 | 0.999915 | 0.999468 | | 0.999943 | 1.000000 | 0.989814 | 0.924876 |
| 5 | B | AVS 2 day 0 | 1.000000 | 0.999999 | 0.998900 | 0.999943 | | 0.937395 | 0.121276 | 0.013809 |
| 6 | B | AVS 2 day 10 | 0.998416 | 0.999990 | 1.00000 | 1.000000 | 0.937395 | | 0.718638 | 0.209107 |
| 7 | B | AVS 2 day 20 | 0.890548 | 0.972845 | 0.998277 | 0.989814 | 0.121276 | 0.718638 | | 0.985128 |
| 8 | B | AVS 2 day 30 | 0.708945 | 0.869503 | 0.971139 | 0.924876 | 0.013809 | 0.209107 | 0.985128 | |

The results for cat urination as set forth below in Tables 29 to 32.

TABLE 29

| Urination at day 0 | Column 1 | Column 2 | Gross total |
|---|---|---|---|
| Effectives line 1 | 5 | 3 | 8 |
| Percentage of total | 33.333% | 20.000% | 53.333% |
| Effectives line 2 | 4 | 3 | 7 |
| Percentage of total | 26.667% | 20.000% | 46.667% |
| Total in column | 9 | 6 | 15 |
| Percentage of total | 60.000% | 40.000% | |
| $Chi^2$ (dl = 1) | 0.04 | p = .8327 | |
| $V^2$ (dl = 1) | 0.04 | p = .8383 | |
| $Chi^2$ Yates corrected | 0.10 | p = .7513 | |
| $Phi^2$ | 0.00298 | | |
| P exact Fisher, unilateral | | p = .6224 | |
| Bilateral | | p = 1.0000 | |
| $Chi^2$ McNemar (A/D) | 0.13 | p = .7237 | |
| $Chi^2$ (B/C) | 0.00 | p = 1.0000 | |

TABLE 30

| Urination at day 10 | Column 1 | Column 2 | Gross total |
|---|---|---|---|
| Effectives line 1 | 2 | 6 | 8 |
| Percentage of total | 13.333% | 40.000% | 53.333% |
| Effectives line 2 | 2 | 5 | 7 |
| Percentage of total | 13.333% | 33.333% | 46.667% |
| Total in column | 4 | 11 | 15 |
| Percentage of total | 26.667% | 73.333% | |
| $Chi^2$ (dl = 1) | .02 | p = .8760 | |
| $V^2$ (dl = 1) | .02 | p = .8802 | |
| $Chi^2$ Yates corrected | .18 | p = .6678 | |
| $Phi^2$ | .00162 | | |
| P exact Fisher, unilateral | | p = .6615 | |
| Bilateral | | p = 1.0000 | |
| $Chi^2$ McNemar (A/D) | 0.57 | p = .4497 | |
| $Chi^2$ (B/C) | 1.13 | p = .2889 | |

TABLE 31

| Urination at day 20 | Column 1 | Column 2 | Gross total |
|---|---|---|---|
| Effectives line 1 | 2 | 6 | 8 |
| Percentage of total | 13.333% | 40.000% | 53.333% |
| Effectives line 2 | 4 | 3 | 7 |
| Percentage of total | 40.000% | 20.000% | 46.667% |
| Total in column | 6 | 9 | 15 |
| Percentage of total | 40.000% | 60.000% | |
| $Chi^2$ (dl = 1) | 1.61 | p = .2049 | |
| $V^2$ (dl = 1) | 1.50 | p = .2207 | |
| $Chi^2$ Yates corrected | 0.55 | p = .4596 | |
| $Phi^2$ | .10714 | | |
| P exact Fisher, unilateral | | p = .2308 | |
| Bilateral | | p = .3147 | |
| $Chi^2$ McNemar (A/D) | 0.00 | p = 1.0000 | |
| $Chi^2$ (B/C) | .10 | p = .7518 | |

TABLE 32

| Urination at day 30 | Column 1 | Column 2 | Gross total |
|---|---|---|---|
| Effectives line 1 | 1 | 7 | 8 |
| Percentage of total | 6.667% | 46.667% | 53.333% |
| Effectives line 2 | 3 | 4 | 7 |
| Percentage of total | 20.000% | 26.667% | 46.667% |
| Total in column | 4 | 11 | 15 |
| Percentage of total | 26.667% | 73.333% | |
| $Chi^2$ (dl = 1) | 1.76 | p = .1847 | |
| $V^2$ (dl = 1) | 1.64 | p = .2001 | |
| $Chi^2$ Yates corrected | .55 | p = .4586 | |
| $Phi^2$ | .11729 | | |
| P exact Fisher, unilateral | | p = .2308 | |
| Bilateral | | p = .2821 | |
| $Chi^2$ McNemar (A/D) | .80 | p = .3711 | |
| $Chi^2$ (B/C) | .90 | p = .3428 | |

With respect to the results concerning inappropriate urination in the home that were recorded by the cats' owners, no significant difference was observed between the treatment and the placebo. The Fisher's exact statistical test was used in this analysis of a bilateral situation. The results are shown below in Table 33.

TABLE 33

| Day | p value |
|---|---|
| T0 (day 0-inclusion visit) | 1.0000 |
| T1 (day 10) | 1.0000 |
| T2 (day 20) | 0.3147 |
| T3 (day 30) | 0.2821 |

The results for aggressiveness as set forth in Tables 34 and 35 below.

TABLE 34

| Aggressiveness at day 10 | Column 1 | Column 2 | Gross total |
|---|---|---|---|
| Effectives line 1 | 5 | 3 | 8 |
| Percentage of total | 33.333% | 20.000% | 53.333% |

TABLE 34-continued

| Aggressiveness at day 10 | Column 1 | Column 2 | Gross total |
|---|---|---|---|
| Effectives line 2 | 5 | 2 | 7 |
| Percentage of total | 33.333% | 13.333% | 46.667% |
| Total in column | 10 | 5 | 15 |
| Percentage of total | 66.667% | 33.333% | |
| $Chi^2$ (dl = 1) | .13 | p = .7144 | |
| V-2 (dl = 1) | .13 | p = .7237 | |
| $Chi^2$ Yates corrected | .03 | p = .8548 | |
| $Phi^2$ | .00893 | | |
| P exact Fisher, unilateral | | p = .5734 | |
| Bilateral | | p = 1.0000 | |
| $Chi^2$ McNemar (A/D) | .57 | p = .4497 | |
| $Chi^2$ (B/C) | .13 | p = .7237 | |

TABLE 35

| Aggressiveness at day 20 | Column 1 | Column 2 | Gross total |
|---|---|---|---|
| Effectives line 1 | 5 | 3 | 8 |
| Percentage of total | 33.333% | 20.000% | 53.333% |
| Effectives line 2 | 4 | 3 | 7 |
| Percentage of total | 26.667% | 20.000% | 46.667% |
| Total in column | 9 | 6 | 15 |
| Percentage of total | 60.000% | 40.000% | |
| $Chi^2$ (dl = 1) | .04 | p = .8327 | |
| V-2 (dl = 1) | .04 | p = .8383 | |
| $Chi^2$ Yates corrected | .10 | p = .7513 | |
| $Phi^2$ | .00298 | | |
| P exact Fisher, unilateral | | p = .6224 | |
| Bilateral | | p = 1.0000 | |
| $Chi^2$ McNemar (A/D) | 0.13 | p = .7237 | |
| $Chi^2$ (B/C) | 0.00 | p = 1.0000 | |

Summary of the Results

The cats treated with a mixture of 11.4% (wt %/wt %) of dimethyl pimelate, 7.8% (wt %/wt %) of dimethyl azelate. 35.6% (wt %/wt %) of methyl palmitate, 95.2% (wt %/wt %) methyl oleate, 11% (wt %/wt %)methyl laurate, 11% (wt %/wt %)methyl myristate, 17% (wt %/wt %)methyl linolate and 11% methyl sterate. 0.5% (wt %/wt %) of this mixture was diluted in 99.5% isopar V showed some ability to limit the aggressive behavior of cats in multi-cat households which have conflicts between the cats. Concerning the diminution of the aggressive behavior which was observed and the level of confidence of the cat owners to leave their cats together in the same room, the results were favorable for treating the cats with a mixture of 11.4% (wt %/wt %) of dimethyl pimelate, 7.8% (wt %/wt %) of dimethyl azelate. 35.6% (wt %/wt %) of methyl palmitate, 95.2% (wt %/wt %) methyl oleate, 11% (wt %/wt %)methyl laurate, 11% (wt %/wt %)methyl myristate, 17% (wt %/wt %)methyl linolate and 11% methyl sterate. 0.5% (wt %/wt %) of this mixture was diluted in 99.5% isopar V. for at least 20 days, where a decrease in aggressiveness was observed with the verum treatment compared to the placebo.

Example 2—Testing of a Different Semiochemical

The semiochemical that was tested in this example was a mixture of 4.5% (w %/w %) methyl laurate, 4.5% (w %/w %) methyl myristate, 13.4% (w %/w %) methyl palmitate, 6.5% (w %/w %) methyl linoeate, 46.5% (w %/w %) methyl oleate, 4.5% (w %/w %) methyl stearate, 11.0% (w %/w %) dimethyl pimelate and 9.0% (w %/w %) dimethyl azelate. 0.5% (wt %/wt %) of this mixture was diluted in 99.5% isopar V.

The same testing was performed on 16 cases of aggressive cat housemates from seven different veterinary clinics as in Example 1. This aggressive behavior was studied with households having 2 or 3 cats that were aggressive among themselves, but not aggressive towards their owner. Furthermore, their aggression did not entail wounding the other cats and the cats were not on any other treatments.

This was a multicenter blinded placebo-controlled study wherein 8 placebos were tested and 8 treatments were tested. At the inclusion visit day 0 (T0) the cat owners were given a diffuser along with instructions for this study that was proposed for 1 month. The evaluation was performed every ten days; day 10, day 20, day 30 (T0, T1, T2, T3) and evaluation was by telephone. A post-treatment evaluation at T4 30 days later after the treatment was stopped was also done by telephone.

Figure 1:
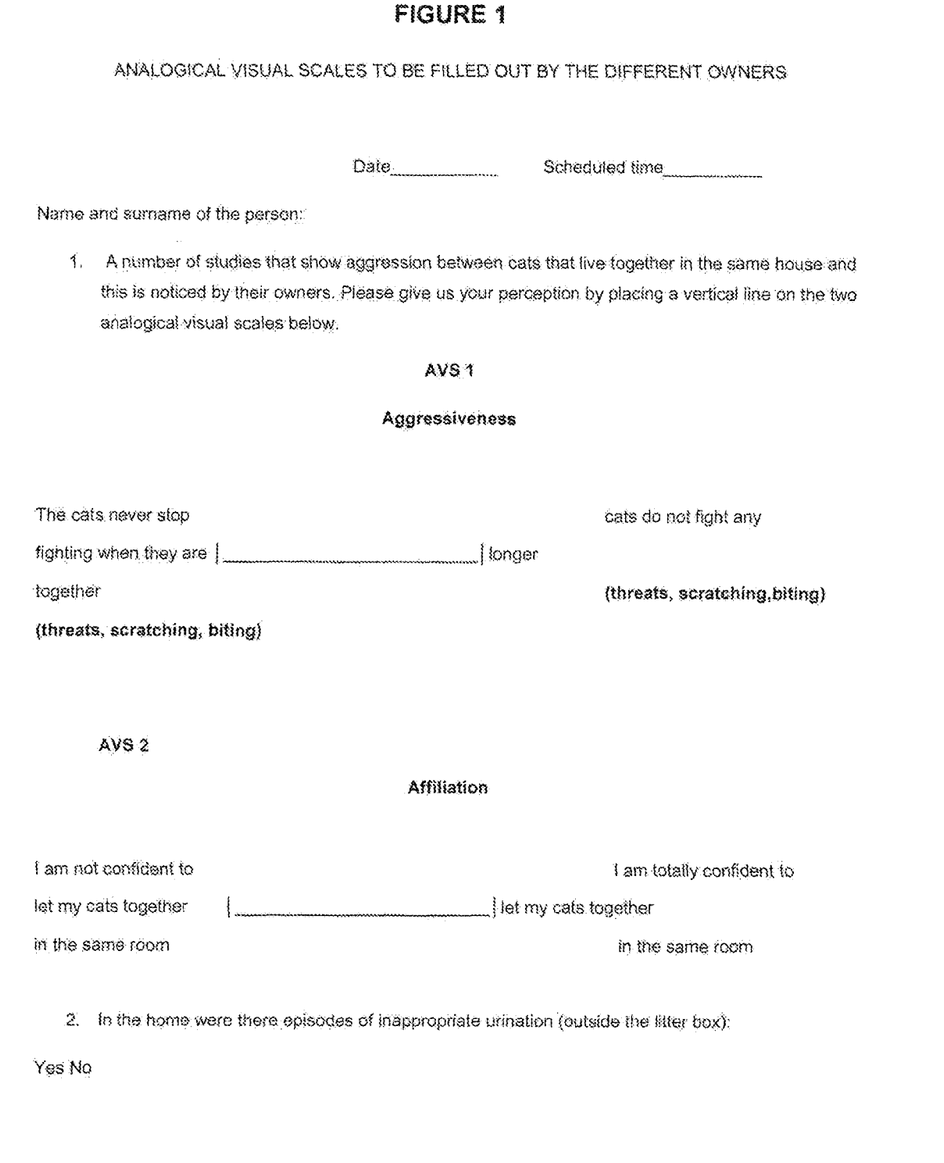
FIG. 1 is a copy of the analogical visual scales that were filled out by the multi-cat owners and submitted at day 0, day 10, day 20 and day 30, which were presented in the analysis in the examples.
Figure 2:
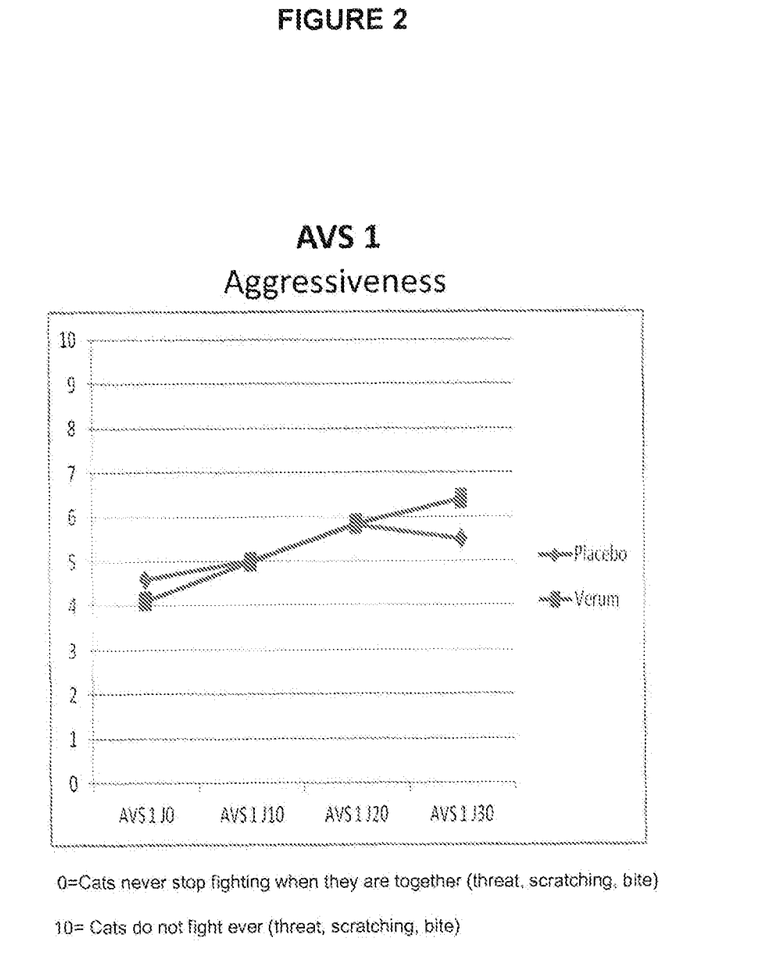
FIG. 2 is a graph showing the final results from the aggressiveness analysis from the study over 30 days. The scale 0 means that the cats never stop fighting when they are together since they threaten, scratch and bite one another.
Figure 3:
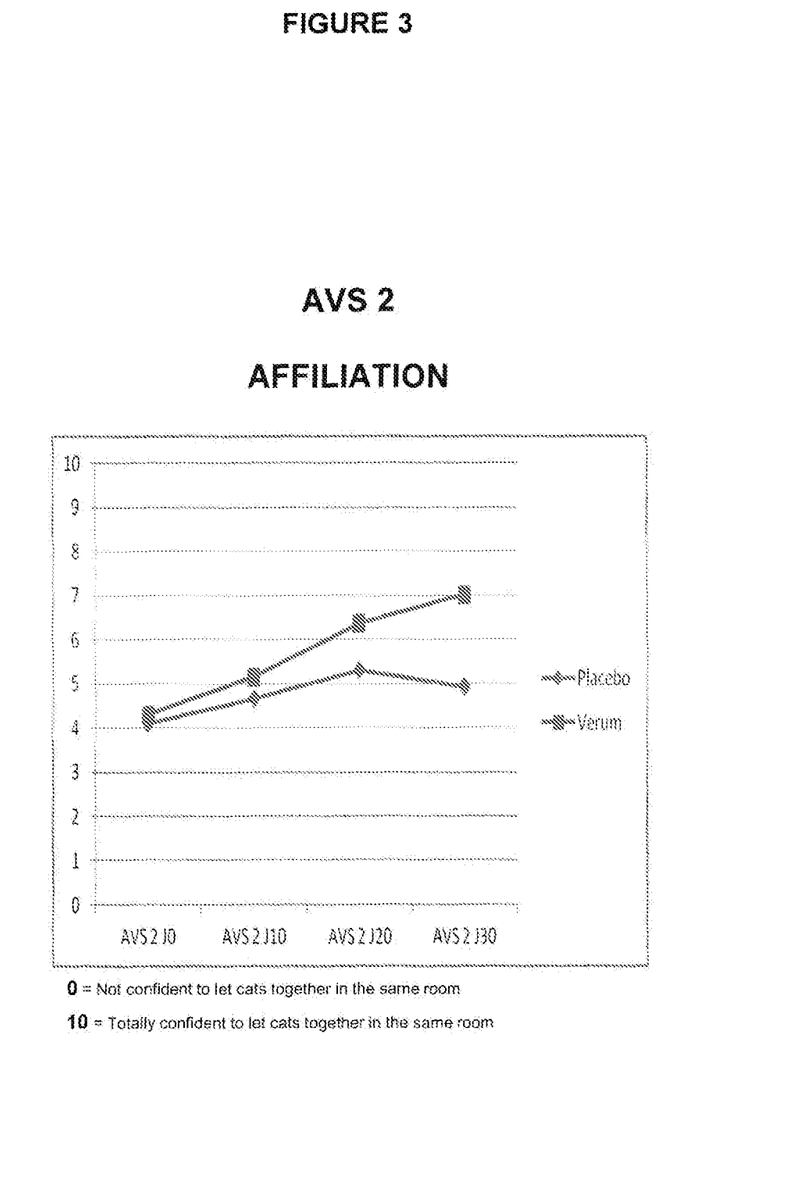
Figure 4:
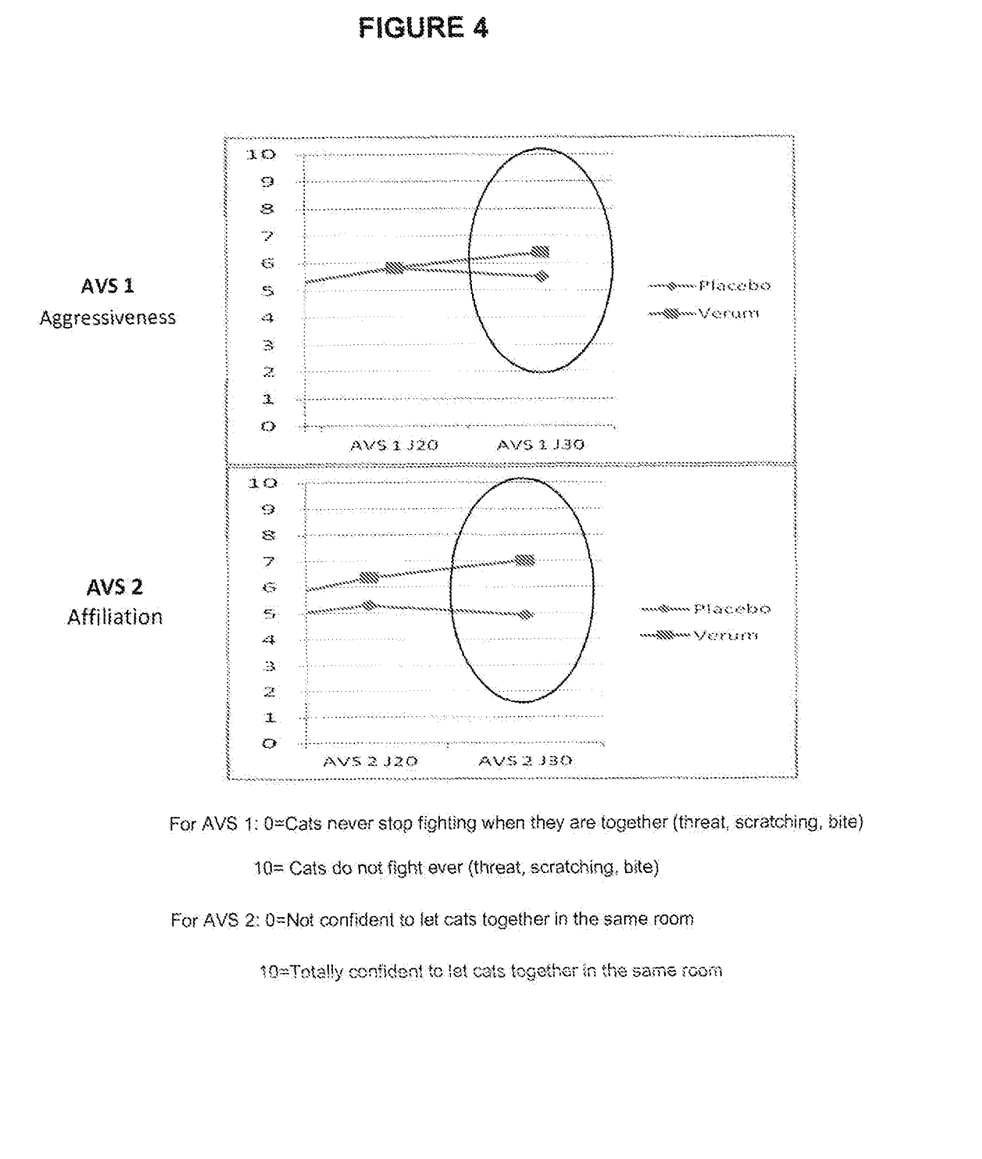
FIG. 4 is a graph showing the final results at day 20 and day 30 for the treated group and the placebo group. At day 30 there was a higher score in the treated group than the placebo group for AVS 1 for aggressiveness and AVS 2 for Affiliation. The means AVS 1 for aggression the treated group was 6.4, while the placebo was 5.5. For the AVS 2 Affiliation group, the mean for the treated was 7.02 and for the placebo was 4.93. At follow up 30 days after the treatment or placebo was discontinued, the owners confirmed that the situation was stable in the treated and placebo groups.

The AVS1 and AVS2 was evaluated in the same manner as in Example 1 using the same form filled out by the owner of the cats.

The results showed that there was a significant improvement between day 0 (T0) and day 30 (T3) in the AVS scores for the treated cats. The AVS 1 (aggression) score for the treated cats under ANOVA statistics was degree of freedom (df)=3; F=4.24; p=0.01. For AVS 2 (affiliation) the score for the treated cats under ANOVA statistics was: df=3; F=5.49; p=0.003. There was no significant difference between the two groups of treatments at day 0 (T0) using the Mann Whitney test; AVS 2 z=0.172 p=0.862.

At day 30 (T3) there was a higher score in the treated group than in the placebo group for the two AVS's (mean AVS 1(aggression) treated=6.4; placebo=5.5; mean AVS 2 (affiliation) treated=7.02; placebo=4.93. As a follow up 30 days after the treatment was discontinued, the owners confirmed that the situation was stable in both the treated group and the placebo group.

Conclusion

These results show that treatment improved social facilitation in multi-cat households with stable results.

Example 3—Testing of a Third Semiochemical

The same testing was performed on cases of aggressive cat housemates as in Example 1. This aggressive behavior was studied with households having 2 or 3 cats that were aggressive among themselves, but not aggressive towards their owner. Furthermore, their aggression did not entail wounding the other cats and the cats were not on any other treatments.

The semiochemical that is tested in this example was a mixture of 15.5% (w %/w %) methyl laurate, 15.5% (w %/w %)methyl myristate, 35.4% (w %/w %)methyl palmitate, 23.5% (w %/w %) methyl linoleate, 74.6% (w %/w %) methyl oleate, 15.5% (w %/w %) methyl stearate, 11.0% (w %/w %) dimethyl pimelate and 9.0% (w %/w %) dimethyl azelate. 0.5% (wt %/wt %) of this mixture was diluted in 99.5% isopar V.

The treatment improved social facilitation and eased aggressiveness in multi-cat households.

While the invention has been described in terms of various preferred embodiments, the skilled artisan will appreciate that various modifications, substitutions, omissions and changes may be made without departing from the scope thereof.

Accordingly, it is intended that the scope of the present invention be limited by the scope of the following claims, including equivalents.

What is claimed is:

1. A semiochemical composition consisting essentially of methyl laurate, methyl myristate, methyl palmitate, methyl linolate, methyl linoleate, methyl stearate, dimethyl pimelate, dimethyl azelate, salts thereof, isomers thereof; or structural analogs thereof that maintain their semiochemical capabilities and mixtures thereof and an acceptable vehicle.

2. The semiochemical composition according to claim 1, wherein said composition consists of between about 1% to 8% (w %/w %) methyl laurate, between about 1% to 8% (w %/w %) methyl myristate, between about 10% to 18% (w %/w %) methyl palmitate, between about 3% to 10% (w %/w %) methyl linoleate, between about 40% to 55% (w %/w %) methyl oleate, between about 1% to 8% (w %/w %) methyl stearate, between about 5% to 15% (w %/w %) dimethyl pimelate, between about 4% to 15% (w %/w %) dimethyl azelate, salts thereof, isomers thereof and/or structural analogs thereof that maintain their semiochemical capabilities and mixtures thereof.

3. The semiochemical composition according to claim 1, wherein said composition consists of between about 2% to 6% (w %/w %) methyl laurate, between about 2% to 6% (w %/w %) methyl myristate, between about 11% to 15% (w %/w %) methyl palmitate, between about 4% to 8% (w %/w %) methyl linoleate, between about 42% to 50% (w %/w %) methyl oleate, between about 2% to 6% (w %/w %) methyl stearate, between about 7% to 13% (w %/w %) dimethyl pimelate, between about 6% to 11% (w %/w %) dimethyl azelate, salts thereof, isomers thereof and/or structural analogs thereof that maintain their semiochemical capabilities and mixtures thereof.

4. A solution consisting of the semiochemical composition according to claim 1 and a solvent.

5. The solution according to claim 4, wherein said solution is in the form of a spray, an aerosol, is administered in a diffuser, is microencapsulated or is a slow release matrix.

6. A method to reduce social conflicts in multi-cat households or for inducing social facilitation in cats said method comprising releasing said semiochemical composition according to claim 1, in an environment surrounding cats.

7. The method according to claim 6, wherein said multi-cat households have at least two cats.

8. The method according to claim 6, wherein said solution is released slowly and occurs between 3 to 5 weeks.

9. The method according to claim 6 wherein said environment is an indoor environment or an enclosed environment.

10. A method to reduce social conflicts in catteries or kennels containing cats said method comprising releasing said semiochemical composition according to claim 1 in an environment surrounding cats.

11. The method according to claim 10, wherein said semiochemical composition or said solution is released slowly and occurs between 3 to 5 weeks.

12. The method according to claim 10, wherein said environment is an indoor environment or an enclosed environment.

13. A method for inducing social facilitation in cats said method releasing said semiochemical composition according to claim 1 in an environment surrounding cats.

14. The method according to claim 13, wherein said semiochemical composition is released slowly and occurs between 3 to 5 weeks.

15. The method according to claim 10, wherein said environment is an indoor environment or an enclosed environment.

16. A method to reduce social conflicts in catteries or kennels containing cats said method comprising releasing said solution of claim 4 in an environment surrounding cats.

* * * * *